(12) United States Patent
Kabra

(10) Patent No.: US 7,795,316 B1
(45) Date of Patent: Sep. 14, 2010

(54) TOPICAL OPHTHALMIC COMPOSITIONS CONTAINING TOBRAMYCIN AND DEXAMETHASONE

(75) Inventor: Bhagwati P. Kabra, Euless, TX (US)

(73) Assignee: Alcon Research, Ltd., Fort Worth, TX (US)

(*) Notice: Subject to any disclaimer, the term of this patent is extended or adjusted under 35 U.S.C. 154(b) by 228 days.

(21) Appl. No.: 11/960,196

(22) Filed: Dec. 19, 2007

(51) Int. Cl.
*A61K 31/70* (2006.01)
*A61K 31/74* (2006.01)

(52) U.S. Cl. .......................... 514/912; 514/40; 424/78; 424/4

(58) Field of Classification Search ................ 514/40, 514/912; 424/78, 4
See application file for complete search history.

(56) References Cited

U.S. PATENT DOCUMENTS

| | | | |
|---|---|---|---|
| 4,136,177 A | | 1/1979 | Lin et al. |
| 4,369,125 A | * | 1/1983 | Kragen et al. ............... 516/107 |
| 5,149,694 A | | 9/1992 | Cagle et al. |
| 6,174,524 B1 | | 1/2001 | Bawa et al. |
| 6,261,547 B1 | | 7/2001 | Bawa et al. |
| 6,352,978 B1 | | 3/2002 | Perdiguer et al. |
| 2002/0019447 A1 | * | 2/2002 | Renn et al. ..................... 516/77 |
| 2005/0169991 A1 | * | 8/2005 | Sanghvi et al. ............. 424/468 |

OTHER PUBLICATIONS

Tako et al., Synergistic interaction between xanthan and guar gum, Carbohydrate Research, 1985,207-213, vol. 138, Issue 2, Elsvier.*
TOBRADEX® Physician's Desk Reference; 34th Edition; p. 209-211; (2006).

* cited by examiner

*Primary Examiner*—Ardin Marschel
*Assistant Examiner*—Zohreh Vakili
(74) *Attorney, Agent, or Firm*—Scott A. Chapple

(57) ABSTRACT

Ophthalmic pharmaceutical compositions containing tobramycin, dexamethasone and deacetylated xanthan gum are described. The compositions provide longer ocular retention for enhanced ocular bioavailability of tobramycin and dexamethasone. In a preferred embodiment, the compositions also provide for improved suspension of dexamethasone. The concentration of ionizable species in the compositions is controlled so as to prevent precipitation of the xanthan gum as a result of ionic interactions between tobramycin and xanthan gum, while allowing for a restoration of viscosity upon topical application of the compositions to the eye. The use of deacetylated xanthan gum is disclosed, so as to avoid formulation instability caused by pH drift during storage.

19 Claims, 5 Drawing Sheets

Viscosity Increase Upon Addition of Sodium Chloride

Viscosity Increase of FID 108536 Upon Increase in pH

Viscosity of FID 108536 Upon Mixing with Phosphate Buffered Saline

Viscosity Increases with Sodium Chloride Equivalent Ionic Concentrations

TOPICAL OPHTHALMIC COMPOSITIONS CONTAINING TOBRAMYCIN AND DEXAMETHASONE

BACKGROUND OF THE INVENTION

The present invention is directed to the field of ophthalmic anti-infective/anti-inflammatory compositions and associated methods of treatment in mammals, particularly humans. More specifically, the present invention is directed to new ocular anti-infective/anti-inflammatory compositions containing tobramycin and dexamethasone.

The use of tobramycin and dexamethasone in combination to treat ophthalmic infections and attendant inflammation is known. Similarly, the use of these compounds in combination to treat inflammation and prophylactically treat (i.e., prevent or ameliorate) infections, such as in conjunction with an ocular surgical procedure, is also known. A product of this type is marketed by Alcon Laboratories, Inc. in the United States and other countries as TOBRADEX® (tobramycin 0.3%/dexamethasone 0.1%) Ophthalmic Suspension. This product has been available in the United States since 1988. It has been widely accepted as being the state-of-the-art ophthalmic anti-infective/anti-inflammatory product for many years. Further details regarding the composition of TOBRADEX® brand ophthalmic suspension are provided in U.S. Pat. No. 5,149,694.

The present invention is directed to the provision of improved tobramycin/dexamethasone compositions for topical ocular application. In particular, the invention is directed to the provision of compositions that contain xanthan gum and have a pH in the range 5 to 6. The viscosities of the compositions at the time of manufacture and during storage in a container prior to use are considerably less than would normally be expected based on the concentrations of xanthan gum utilized. This lowering of the viscosity prior to use is advantageous relative to dispensing of the compositions from a dropper bottle (e.g., DROPTAINER™, Alcon Laboratories, Inc.) or other container when administering the compositions to a patient. The reduction of the viscosities of the compositions at the time of manufacture and during storage prior to application to the eye is attributable to ionic interactions between the tobramycin and xanthan gum which occur at a pH of 5 to 6. Those interactions, if left uncontrolled, lead to the formation of clumps of tobramycin and xanthan gum and/or precipitation of the xanthan gum. The present invention is based in part on the discovery of formulation components and parameters that have been shown to be effective in controlling the tobramycin/xanthan gum interactions.

As indicated above, the compositions of the present invention contain xanthan gum. The use of xanthan gum as a component of ophthalmic compositions is described in U.S. Pat. No. 4,136,177; U.S. Pat. No. 6,352,978; U.S. Pat. No. 6,174,524; and U.S. Pat. No. 6,261,547. The '978 patent describes the use of xanthan gum in combination with tobramycin. It indicates that xanthan gum and tobramycin are incompatible at a pH of 5.0 to 7.8, and teaches that this incompatibility problem can be avoided by formulating tobramycin/xanthan gum compositions to have a pH in the range of 7.9 to 8.6. A product based on the invention described in the '978 patent is marketed by affiliates of Alcon Laboratories, Inc. in Europe and several other countries.

The '524 and '547 patents describe xanthan-based ophthalmic compositions formulated as non-gelled liquids that gel upon topical application to the eye. The compositions of the '524 and '547 patents are formulated so that their total ionic strength is approximately 120 mM or less, and preferably about 94 mM or less. The compositions of the '524 and '547 patents that have a total ionic strength greater than about 120 mM do not gel upon contact with the eye. The compositions of '524 and '547 patents are generally viscous and gel upon topical application to the eye. In contrast, the compositions of the present invention generally have lower viscosities in the bottle, but the viscosities increase significantly following application to the eye, as interactions between tobramycin and xanthan gum are broken down.

The tobramycin/dexamethasone compositions of the present invention are formulated at a pH of 5 to 6. This pH range is necessary in order to maintain the stability of dexamethasone. The use of a pH in this range for an ophthalmic tobramycin/dexamethasone composition is described in U.S. Pat. No. 5,149,694. TOBRADEX® (tobramycin 0.3%/dexamethasone 0.1%) Ophthalmic Suspension also has a pH in this range.

The present invention resulted from an effort to create improved tobramycin/dexamethasone formulations, particularly compositions that provide for enhanced bioavailability of tobramycin and/or dexamethasone upon topical application to the eye, via the use of xanthan gum as a vehicle for tobramycin and dexamethasone. However, as described above, it was discovered that ionic interactions between tobramycin and xanthan gum at a pH of 5 to 6 lead to clumping and/or precipitation of the xanthan gum. In addition, it was discovered that xanthan gum slowly undergoes deacetylation during storage, thereby resulting in a stability problem. As explained in greater detail below, the present invention is based on the discovery of solutions to these problems.

SUMMARY OF THE INVENTION

The present invention is directed to the provision of improved pharmaceutical compositions that contain tobramycin and dexamethasone and are suitable for topical application to the eyes of human patients. The compositions of the present invention are based in-part on the discovery of formulation parameters that control ionic interactions between tobramycin and xanthan gum, while maintaining the stability of dexamethasone. The control of those interactions has enabled the present inventors to provide compositions having physical properties that are very advantageous. More specifically, the compositions of the present invention have advantageous rheological properties, as a result of the controlled interactions between tobramycin and xanthan gum, and those properties enhance the bioavailability of drugs administered topically to the eye, particularly tobramycin and dexamethasone. In addition, the compositions provide significant improvements relative to the suspension of relatively insoluble forms of dexamethasone therein (i.e., dexamethasone alcohol), such that even if a patient occasionally fails to comply with instructions to shake a bottle containing the compositions prior to application to the eye, the availability of dexamethasone suspended in the compositions is not significantly diminished.

Solutions or suspensions containing xanthan gum at the concentrations utilized in the present invention are normally very viscous. As explained in greater detail below, the present invention is based in part on the finding that tobramycin, which is a cationic molecule, interacts ionically with the negatively charged xanthan gum molecules, thereby lowering the viscosity of the compositions. Upon application to the eye, the viscosity of the tobramycin/xanthan gum compositions of the present invention is restored (i.e., increases), as a result of disruption of the ionic interactions between tobramycin and xanthan gum, thereby resulting in increased ocular retention and enhanced ocular bioavailability. However, during manufacture of the compositions, as well as during storage of the compositions prior to use, the ionic interactions between tobramycin and xanthan gum must be controlled, so as to avoid the formation of precipitates and clumping, and maintain a uniform dispersion of the xanthan gum in the compositions. The present invention is based in-part on the identification of formulation features and parameters that control the ionic interaction between tobramycin and xanthan gum during the manufacturing and storage phase while maintaining the stability of dexamethasone.

Tobramycin is a positively charged molecule, while xanthan gum is negatively charged. When combined in an aqueous solution or suspension at an acidic pH, the tobramycin will cause the xanthan gum to precipitate or form clumps. Such precipitation or clumping is unacceptable in two respects. First, the tobramycin and xanthan gum are no longer uniformly distributed in the composition. This is unacceptable because each drop of the composition, upon dispensing from a suitable bottle or other container, must provide a uniform and predictable amount of the components of the composition, particularly the active ingredients. Second, the precipitation or clumping effect of tobramycin on xanthan gum results in a loss of the viscosity-enhancing effect of the xanthan gum on the composition, such that the viscosity of the composition may revert to a value equivalent to water (i.e., about 1 centipoise).

U.S. Pat. No. 6,352,978 is based in-part on the discovery that these ionic interactions may be controlled by utilizing an alkaline pH (i.e., a pH of 8.0 or greater). However, the use of an alkaline pH is not possible in the tobramycin/dexamethasone compositions of the present invention, because dexamethasone is not stable at this pH level. Dexamethasone is stable at a pH of 5 to 6, but at this pH the negatively charged xanthan gum and positively charged tobramycin interact to form precipitates and/or agglomerated clumps of material.

The present inventors have discovered that the above-discussed problems can be overcome by utilizing ionic species to control the ionic interaction between tobramycin and xanthan gum, so as to avoid formation of precipitates or clumps and maintain the viscosity of the present tobramycin/dexamethasone suspensions or solutions within an acceptable range prior to application to the eye. This control is achieved via inclusion of ionic species that associate with xanthan gum or tobramycin, thereby reducing direct interactions between these compounds. The ionic species utilized for this purpose can be any pharmaceutically acceptable agents that dissociate into anions and cations at a pH in the range of 5 to 6, but preferably are inorganic electrolytes or organic buffering agents, such as sodium chloride, potassium chloride or sodium sulfate.

Upon application to the eye, the viscosity of compositions of the present invention is restored, due to disruption of the complexes between xanthan gum and tobramycin. That is, upon application to the eye, the viscosity of the compositions of the present invention rises, thereby increasing the length of time during which compositions are retained on the corneal surface and enhancing ocular bioavailability. For example, as a result of this enhanced ocular bioavailability, it has been determined that a dexamethasone concentration of only 0.05 w/v % in the compositions of the present invention is bioequivalent to a dexamethasone concentration of 0.1 w/v % in TOBRADEX® Ophthalmic Suspension.

The present invention is also based in-part on the discovery that the xanthan gum-based compositions of the present invention possess superior suspension properties. More specifically, dexamethasone particles remain suspended in the compositions of the present invention significantly longer, relative to the prior TOBRADEX® formulation. This improvement provides important advantages, particularly with respect to patients who sometimes forget or overlook the instructions to "shake well before using" that apply to all ophthalmic suspension compositions.

The present invention is also based in-part on a finding that xanthan gum is much more effective as a viscosity enhancing agent in the compositions of the present invention if it is at least partially deacetylated. More specifically, xanthan gum slowly undergoes deacetylation in aqueous solutions. It has been determined that such deacetylation further lowers the pH of the compositions, thereby increasing ionic interactions between tobramycin and dexamethasone. These interactions initially result in a loss of viscosity and ultimately cause clumping and/or precipitation of xanthan gum and tobramycin. The present inventors have determined that this problem can be overcome by deacetylating xanthan gum prior to its inclusion in the compositions of the present invention.

DESCRIPTION OF PREFERRED EMBODIMENTS

Figure 1:
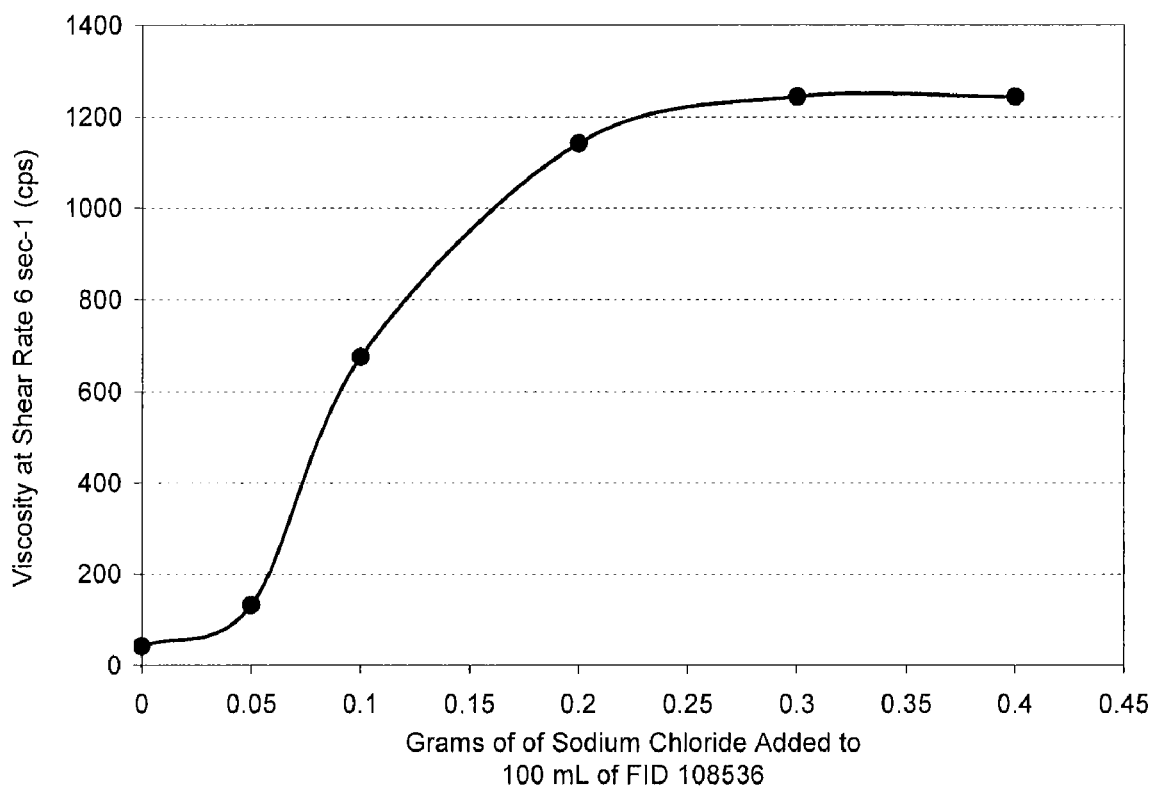
FIG. 1 is a graph showing the effect of sodium chloride concentration on the viscosity of a representative formulation of the present invention, as described in Example 3.

The compositions of the present invention are formulated as sterile aqueous suspensions comprising tobramycin at a concentration of 0.1 to 0.5 weight/volume percent (w/v %), preferably 0.3 w/v %; dexamethasone at a concentration of 0.03 to 0.1 w/v %, preferably 0.05 w/v %; an aqueous vehicle containing deacylated xanthan gum at a concentration of 0.3 to 0.9 w/v %, preferably 0.6 w/v %; and ionic species in an amount sufficient to limit interactions between tobramycin and xanthan gum, such that the viscosity of the suspensions is maintained within the range of 10 to 700 centipoise ("cps") preferably 10 to 300 cps, for a period of 18 months subsequent to the date of manufacture. The suspensions have a pH in the range of 5 to 6.

The ionic species utilized in the present invention can be any pharmaceutically acceptable compound that dissociates into cationic and anionic components at a pH in the range of 5 to 6. The compounds may be inorganic or organic, but will preferably be inorganic electrolytes, organic buffering agents or combinations thereof. Examples of such ionic species include sodium chloride, potassium chloride, calcium chloride, magnesium chloride, sodium sulfate, sodium citrate, potassium citrate, sodium phosphate, potassium phosphate, sodium acetate, sodium borate, boric acid/mannitol complexes, boric acid/sorbitol complexes and combinations thereof.

The total amount of ionizable species present in the compositions of the present invention affects the viscosity of the compositions. The compositions must contain one or more ionizable compounds in an amount sufficient to reduce or preclude ionic interactions between tobramycin and xanthan gum, such that the formation of precipitates or clumping in the compositions is avoided, without exceeding the viscosity ranges specified above. The compositions therefore must contain ionic species in an amount sufficient to provide the compositions with a viscosity at the time of manufacture (referred to herein as "initial viscosity") of at least 10 cps, preferably an amount sufficient to provide an initial viscosity of 15 cps or greater, and most preferably an amount sufficient to provide an initial viscosity of 25 cps or greater. The initial viscosity of the compositions is preferably in the range of 25 to 175 cps.

The effect of ionic species on ionic strength and viscosity is dependent on the particular ionic species selected. For example, the effect of sodium sulfate on ionic strength and viscosity is about 5.3 times greater than the effect of sodium chloride. The relative effect of different ionized salts maybe determined by means of routine experimentation, within the pH range, tobramycin concentrations, xanthan gum concentrations and viscosity ranges specified herein. The only critical parameters, so far as the compositions of the present invention is concerned, is that the amount of ionizable salts must be sufficient to avoid formation of precipitates or clumping of tobramycin and xanthan gum, without elevating the viscosity of the composition above 700 cps or, more preferably, 300 cps.

The viscosities of the ophthalmic suspensions of the present invention may increase somewhat over time, due to loss of moisture from the compositions. The suspensions are therefore formulated so as to maintain the viscosities thereof within the range of 10 to 700 cps, preferably 10 to 300 cps, over a period of 18 months. The viscosity of the compositions of the present invention from the time of manufacture until application to the eye is referred to herein as the "in vitro viscosity" of the compositions.

The viscosity values expressed herein are based on the use of a Brookfield viscometer at a shear rate of approximately 6 sec$^{-1}$ and at a temperature of 25° C. A shear rate of approximately 6 sec$^{-1}$ can be achieved using spindle CP-52 at 3 revolutions per minute ("rpm"), spindle CP-51 at 1.5 rpm, spindle CP-42 at 1.5 rpm or spindle CP-41 at 3 rpm. Spindles CP-52 and CP-51 are typically used to measure viscosities greater than 300 centipoise ("cps"). Spindles CP-42 and CP-41 are generally typically used to measure viscosities less than 300 cps.

As indicated above, the viscosity of the compositions of the present invention is restored upon application to the eye, such that the viscosity of a composition following topical ocular administration is greater than its viscosity while stored in a container, following manufacture and prior to application to the eye. This increase is caused by a shift in the pH and ionic strength of the compositions when a small amount thereof (i.e., one or two drops) comes into contact with the lacrimal fluid of human eyes (i.e., tears). That is, the electrolytes in the lacrimal fluid raise the pH and ionic strength of the compositions, which causes the viscosity of the compositions to increase, thereby enhancing the ocular retention and bioavailability of the compositions.

It is not readily possible to measure the viscosity of the compositions of the present invention in vivo, i.e., following application to the eye. However the simulated in vivo viscosity model described below can be utilized to evaluate the effect of lacrimal fluid on the viscosity of the compositions of the present invention in vivo. The viscosity of the compositions of the present invention in vivo (i.e., following topical application to the eye) is simulated by adding a small amount of the following phosphate-buffered saline solution to the compositions:

| Phosphate-Buffered Saline Solution Utilized for Simulated In Vivo Viscosity Measurements | |
|---|---|
| Ingredient | Amount (w/v %) |
| Dibasic Sodium Phosphate (anhydrous) | 0.57% |
| Monobasic Sodium Phosphate Monohydrate | 0.08% |
| Sodium Chloride | 0.65% |
| Purified Water | QS to 100% |
| pH | 7.4 |

The addition of the above-described phosphate-buffered saline solution ("PBS solution") to the compositions of the present invention simulates the effect of lacrimal fluid on the viscosity of the compositions. The PBS solution is added to the compositions at a ratio of 1 to 10, i.e., one part PBS solution per ten parts of the tobramycin/dexamethasone/xanthan gum compositions of the present invention.

For purposes of the present specification, the actual in vivo viscosity for a composition of the present invention is presumed to be the same as the simulated in vivo viscosity for such composition. All references to "in vivo viscosity" herein are therefore interchangeable with "simulated in vivo viscosity". All references herein to "simulated in vivo viscosity" and "in vitro/in vivo viscosity ratio" are based on the use of the above-described viscosity measurement procedures and simulated in vivo viscosity model.

The ratio of the viscosity of a composition of the present invention prior to application to the eye to the viscosity of the same composition following application of one drop thereof to the eye is referred to herein as the "in vitro/in vivo viscosity ratio". The compositions of the present invention preferably have an in vitro/in vivo viscosity ratio in the range of from $$\frac{1}{100} \text{ to } \frac{65}{100}$$

or 0.01 to 0.65.

The foregoing ratio may also be expressed in terms of percentages, i.e., the in vitro viscosity divided by the simulated in vivo viscosity multiplied by 100. The foregoing range for the ratio of in vitro to simulated in vivo viscosity is therefore equivalent to a range wherein the in vitro viscosity of a composition of the present invention is from 1% to 65% of the simulated in vivo viscosity of said composition.

The relative viscosity values may also be expressed as a ratio of in vivo viscosity to in vitro viscosity. The compositions of the present invention preferably have an in vivo/in vitro viscosity ratio of $$\frac{100}{1} \text{ to } \frac{100}{65},$$

which is equivalent to a range wherein the in vivo viscosity of a composition is from about 1.5 to 100 times greater than the in vitro viscosity of said composition.

The tobramycin, dexamethasone and xanthan gum utilized in the sterile ophthalmic suspensions of the present invention are known compounds and are readily available from various sources. A non-salt form of dexamethasone, such as dexamethasone alcohol, is preferred. However, a salt form of dexamethasone, such as dexamethasone sodium phosphate, can also be utilized. When a dexamethasone salt is selected, the ionic strengths contributed by the ions formed upon dissociation of the dexamethasone salt must be considered when determining the concentrations of ionizable species required to control the ionic interactions between tobramycin and xanthan gum.

A pharmaceutical grade of xanthan gum should be utilized. The xanthan gum should preferably be polish-filtered prior to use. The selection of appropriate filtering techniques can be readily determined by a person skilled in the art. As discussed above, the xanthan gum must be deacetylated, so as to enhance the stability of the suspensions of the present invention during storage. The acetate content of xanthan gum is based on the acetate bound to the xanthan gum. The acetate content is typically expressed as a percent of xanthan gum, based on weight. The xanthan gum raw material will typically have up to 6% bound acetate. The deacetylated xanthan gum utilized in the present invention contains less than 2% bound acetate, and preferably less than 1% bound acetate. The importance of deacetylating xanthan gum and a process by which deacetylation may be performed are further explained in Examples 1 and 2, below.

As indicated above, the compositions of the present invention have a pH of from 5 to 6. The compositions will also have an ophthalmically acceptable osmolality, which is typically in the range of 200 to 400 milliOsmoles per kilograms of water (mOsm/kg). When selecting buffering agents suitable for maintaining the pH of the compositions within the specified range of 5 to 6 and/or selecting an osmolality-adjusting agent, the impact of such agents on the ionizable species content of the compositions must be considered. For example, if the addition of sodium chloride for purposes of adjusting osmolality increases the ionic species concentration beyond a level that is acceptable (i.e., relative to the targeted viscosity value), it may be necessary to replace all or part of the sodium chloride with a non-ionic osmolality-adjusting agent, such as propylene glycol.

The compositions of the present invention may contain various other ingredients that are typically utilized in ophthalmic pharmaceutical compositions, such as antimicrobial preservatives (e.g., benzalkonium chloride) and wetting agents (e.g., tyloxapol and Polysorbate 80). The compositions are preferably formulated and packaged as multi-dose products, but may also be formulated without a conventional antimicrobial preservative and packaged in a sealed, unit dose vial.

The compositions of the present invention are useful in the treatment of ocular inflammatory conditions wherein either an infection or a risk of infection exists. As utilized herein, the term "treatment" encompasses both active treatment of an existing condition and prophylactic treatment of a patient that is at risk of developing a condition (e.g., infection). The compositions of the present invention are particularly useful in treating ocular inflammation associated with injuries to the eye resulting from trauma, as well as inflammation associated with ocular surgical procedures (e.g., cataract surgery, retinal surgery, LASIK surgery) and ocular injections (e.g., retrobulbar injections, posterior juxtascleral injections and anterior juxtascleral injections).

Such treatments can be performed by applying a small amount (e.g., one to two drops) of a composition of the present invention to the affected eye or eyes of a patient from two to four times per day. However, both the amount of the dose and the dosing frequency may be modified by clinicians.

Example 1

The preparation of tobramycin/dexamethasone/xanthan gum formulations utilizing xanthan gum that has not bee deacetylated is described below. The stability of the resulting formulations was also evaluated, as explained below.

Preparation of Xanthan Gum Stock Solution

Hot water was added to a vessel. Xanthan gum was weighed and slowly added to the vessel while mixing. The temperature was adjusted to 60° C. and the xanthan gum and water were mixed until uniform. Purified water was added to bring the composition to the final target weight and mixed until uniform. The temperature was increased to 70° C. prior to filtering through an appropriate polishing filter e.g., 1.2 um filter.

Preparation of Tobramycin/Dexamethasone Formulations Using Xanthan Gum Stock Solution The amounts of tobramycin, sodium chloride, boric acid and disodium edetate specified in Table 1A below were added to a portion of the purified water and dissolved. Hydrochloric or sulfuric acid was added to reduce pH. Tyloxapol and dexamethasone were added as slurry or as powder. Batch quantity of xanthan gum stock solution was added and mixed well. 1N hydrochloric acid or 1N sulfuric acid were added to reach the target pH. Purified water was added to bring to final volume and mixed well. The viscosities of the resulting formulations were measured at a shear rate of 6 $\text{sec}^{-1}$. The respective viscosity values are shown in Table 1A below.

TABLE 1A

| | Formulation Number | |
| --- | --- | --- |
| | 107201 W/V % | 107209 W/V % |
| INGREDIENTS | | |
| Tobramycin | 0.3 | 0.3 |
| Dexamethasone | 0.1 | 0.1 |
| Xanthan Gum | 0.9 | 0.9 |
| Sodium chloride | 0.42 | 0.08 |
| Tyloxapol | 0.05 | 0.05 |
| Boric Acid | 0.5 | 1 |
| Disodium Edetate | 0.01 | 0.01 |
| Sodium Hydroxide | Adjust pH to 5.5 | Adjust pH to 5.7 |
| Hydrochloric Acid | Adjust pH to 5.5 | None |
| Sulfuric Acid | None | Adjust pH to 5.7 |
| Purified Water | Qs to 100% | Qs to 100% |
| RESULTS | | |
| Viscosity at shear rate 6 sec-1 (cps) | 418 | 642 |

The formulations described in Table 1A were subjected to accelerated stability testing. As shown in Table 1B, below, the pH and viscosities of the formulations, which were prepared using xanthan gum that has not been deacetylated, decrease upon storage. This eventually makes the formulations unusable. Specifically, the uniform nature of the suspensions was lost.

TABLE 1B

Stability of pH and Viscosity of Tobramycin/Dexamethasone Formulations
Prepared Using Non-Deacetylated Xanthan Gum

| Analysis | Formulation Number | | | |
|---|---|---|---|---|
| | 107201 | 107209 | 107201 | 107209 |
| | pH | | Viscosity of Formulation (cps) | |
| Initial | 5.48 | 5.74 | 418 | 642 |
| 40° C., 4 Weeks | 5.33 | 5.56 | 187 | 217 |
| 40° C., 8 Weeks | 5.08 | 5.36 | 86 | 141 |
| 40° C., 16 Weeks | 4.86 | 4.89 | 25 | 37 |
| 50° C., 1 Week | 5.37 | 5.73 | 175 | 240 |
| 50° C., 2 Weeks | 5.20 | 5.25 | 95 | 160 |
| 50° C., 4 Weeks | 5.10 | 5.14 | 48 | 91 |
| 50° C., 8 Weeks | 4.70 | 4.81 | Not Uniform | Not Uniform |
| 60° C., 1 Week | 5.20 | 5.16 | 68 | 132 |
| 60° C., 2 Weeks | Not Uniform | 4.83 | Not Uniform | 43 |
| 60° C., 4 Weeks | Not Uniform | Not Uniform | Not Uniform | Not Uniform |

Example 2

The preparation of tobramycin/dexamethasone formulations in accordance with the principles of the present invention, including the use of deacetylated xanthan gum, is described below.

Preparation of Xanthan Gum Stock Solution and Pretreatment with Base

Hot water was added to a vessel. Xanthan gum was weighed and slowly added to the vessel while mixing. 2.5 ml of 1 N NaOH or equivalent per 1 g of xanthan gum was added and then mixed for 20 minutes. 1.66 ml of 1N HCl or equivalent per 1 g of xanthan gum was then added. Purified water was added to adjust the target weight followed by mixing for 15 minutes. The deacetylated xanthan gum was then filtered through an appropriate filter e.g., 1.2 um filter.

Preparation of a Tobramycin/Dexamethasone Formulation Using Pre-Treated Xanthan Gum Stock Solution The specified amounts of tobramycin, sodium chloride, sodium sulfate, disodium edetate, and propylene glycol were added to a portion of the purified water, following by addition of tyloxapol and dexamethasone as a slurry or as powder. The pH was adjusted using 1 N hydrochloric acid to a pH slightly higher than the target pH. The deacetylated xanthan gum stock solution described above was then added and the resulting suspension was mixed well. The pH was adjusted with HCl and/or NaOH solution to the target level and the viscosity of the formulation was measured.

TABLE 2A

| | Formulation Number 108536 W/V % |
|---|---|
| INGREDIENTS | |
| Tobramycin | 0.3 |
| Dexamethasone | 0.1 |
| Xanthan Gum | 0.6 |
| Sodium chloride | 0.24 |
| Propylene Glycol | 0.6 |
| Tyloxapol | 0.05 |
| Sodium Sulfate (Anhydrous) | 0.25 |
| Disodium Edetate | 0.01 |
| Benzalkonium Chloride | 0.01 |

TABLE 2A-continued

| | Formulation Number 108536 W/V % |
|---|---|
| Sodium Hydroxide | Adjust pH to 5.75 |
| Hydrochloric Acid | Adjust pH to 5.75 |
| Purified Water | Qs to 100% |
| RESULTS | |
| Viscosity at shear rate 6 sec-1 (cps) | 116 |
| Simulated In Vivo Viscosity at shear rate 6 sec-1 (cps) | 1059 |
| Viscosity of Formulation as a % of Simulated In Vivo Viscosity | 11% |

As shown in Table 2B, below, the pH values for Formulation 108536, which contains is deacetylated xanthan gum, were fairly stable upon storage, unlike that of Formulations 107201 and 107209 in Example 1. As a result, the viscosities of Formulation 108536 remained stable or increased during storage, rather than decreasing, as in Example 1.

TABLE 2B

Stability of pH and Viscosity of Tobramycin/Dexamethasone Formulations
Prepared Using Deacetylated (Pre-treated) Xanthan Gum

| | Formulation Number 108536 | |
|---|---|---|
| Analysis | pH | Pre-dose Viscosity (cps) |
| Initial | 5.84 | 116 |
| 40° C., 4 Weeks | 5.80 | 166 |
| 40° C., 8 Weeks | 5.81 | 167 |
| 40° C., 12 Weeks | 5.81 | 181 |
| 40° C., 16 Weeks | ND | ND |
| 40° C., 26 Weeks | ND | ND |
| 50° C., 1 Week | ND | ND |
| 50° C., 2 Weeks | 5.79 | 152 |
| 50° C., 4 Weeks | 5.78 | 179 |
| 50° C., 8 Weeks | 5.76 | 271 |
| 50° C., 12 Weeks | 5.73 | 372 |
| 50° C., 16 Weeks | ND | NA |
| 60° C., 1 Week | 5.79 | 150 |
| 60° C., 2 Weeks | 5.78 | 172 |
| 60° C., 3 Weeks | ND | ND |
| 60° C., 4 Weeks | 5.66 | 235 |

ND = Not Determined

Example 3

The effect of tobramycin on the initial viscosity of the compositions of the present invention and the recovery of viscosity upon application of the compositions to the eye are further illustrated herein. The formulation shown in Table 3A below, which is a different lot of Formulation Number 108536 described in Table 2A above and is representative of the compositions of the present invention, was prepared is utilizing deacetylated xanthan gum. The initial viscosity of the formulation was measured at a shear rate of 6 sec$^{-1}$ and determined to be 42 cps.

TABLE 3A

| Component | % w/v | Function |
|---|---|---|
| Tobramycin | 0.3 | Active |
| Dexamethasone (Micronized) | 0.1 | Active |

TABLE 3A-continued

| Component | % w/v | Function |
|---|---|---|
| Benzalkonium Chloride | 0.01 | Preservative |
| Tyloxapol | 0.05 | Wetting Agent |
| Disodium Edetate | 0.01 | Preservation Aid |
| Sodium Chloride | 0.23 ± 0.04 | Tonicity Agent |
| Sodium Sulfate | 0.25 | Tonicity Agent |
| Xanthan Gum | 0.6% | Viscosity Modifier |
| Propylene Glycol | 0.6 | Tonicity Agent |
| Hydrochloric Acid and/or Sodium Hydroxide | Adjust pH to 5.7 | pH Adjustment |
| Purified Water | QS 100 | Vehicle |

A second formulation, which was identical to the formulation shown in Table 3A, except for the omission of tobramycin, was also prepared. The second formulation was determined to have an initial viscosity of 836 cps.

Figure 2:
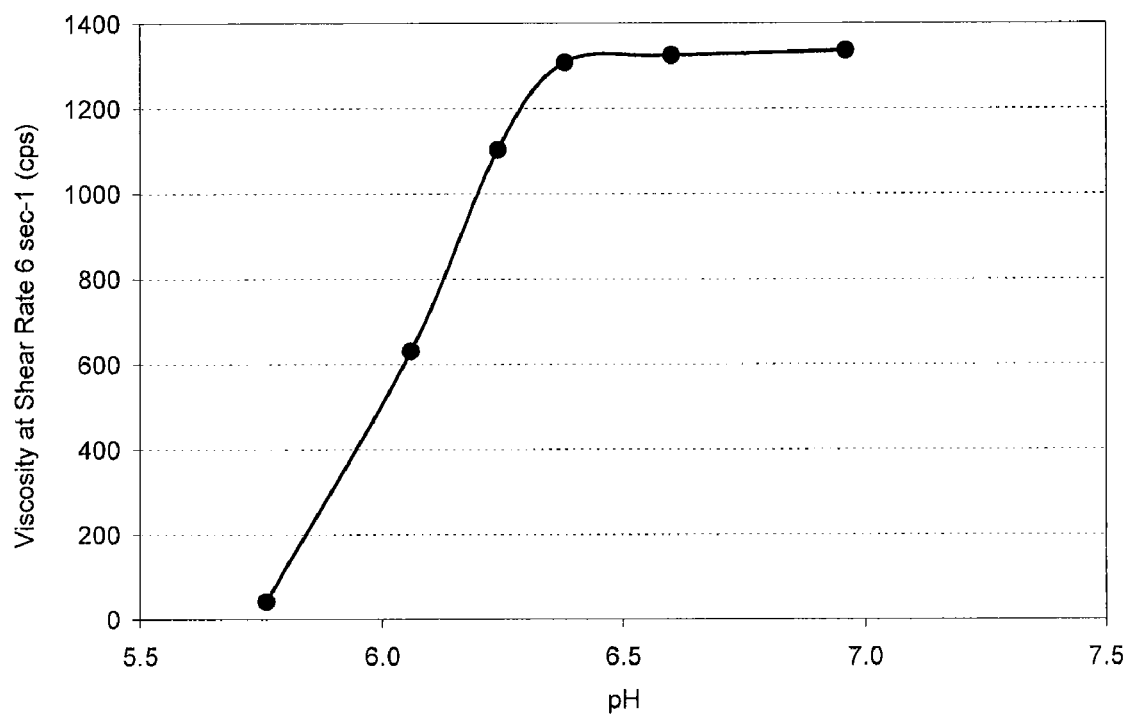
FIG. 2 is a graph showing the effect of pH on the viscosity of a representative formulation of the present invention, as described in Example 3.
Figure 3:
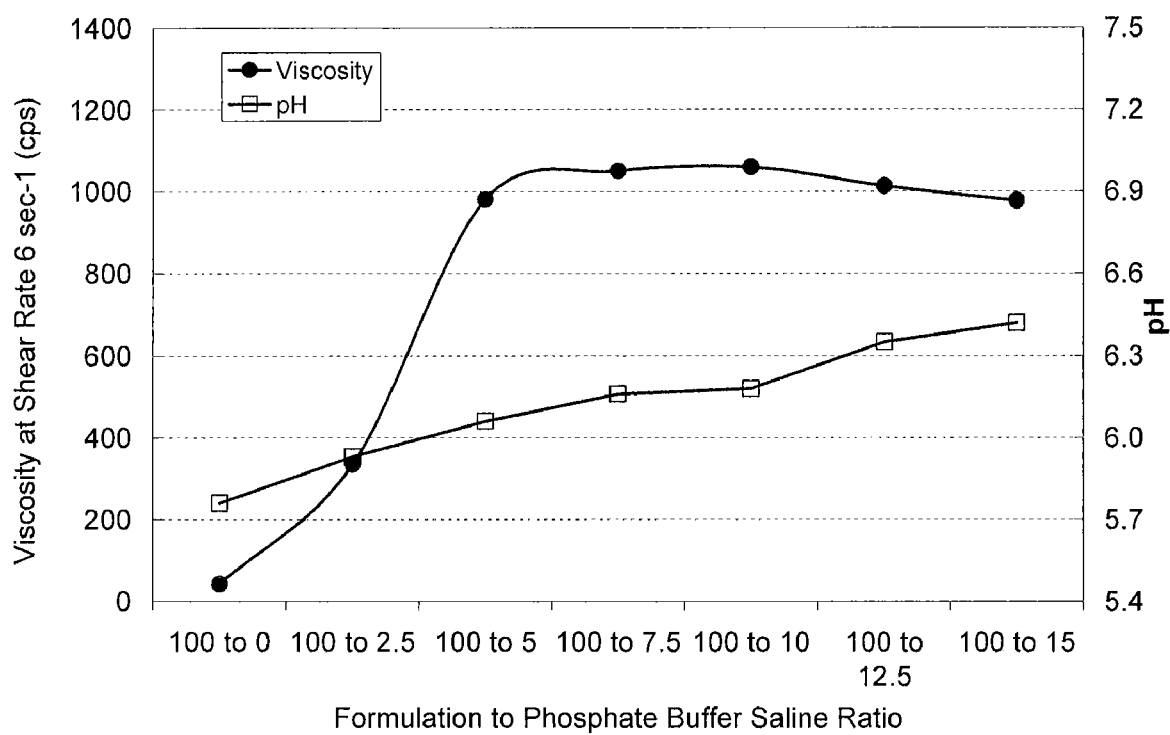
FIG. 3 is a graph showing the effect of a phosphate-buffered saline solution having a pH of 7.4 on the viscosity of a representative formulation of the present invention, as described in Example 3.

A slight increase in pH or addition of small amount of ions (e.g. sodium chloride, phosphate buffer) reduces the ionic interactions between tobramycin and xanthan gum, thereby restoring the formulation viscosity. This phenomenon is graphically presented in FIGS. 1-3. FIG. 1 shows that the viscosity of the formulation described in Table 3A increases from 42 cps to over 1,000 cps upon addition of 0.2 g of sodium chloride to 100 mL of the formulation. FIG. 2 shows is that the viscosity of the formulation increases from 42 cps at pH 5.7 to over 1,100 cps when pH is adjusted upward to 6.2, and to 1,300 cps when pH is at 6.4. FIG. 3 shows that the viscosity of the formulation increases from 42 cps to 1,059 cps upon addition of 10 mL of the above-described PBS solution to 100 mL of the suspension.

When tobramycin was removed from the formulation shown in Table 3A, the viscosity of the formulation did not increase after mixing with the PBS solution. Specifically, a modified version of the formulation, without tobramycin, was determined to have a viscosity of 667 cps when 10 ml of phosphate buffered saline solution was added to 100 ml of the formulation. In other words, the viscosity of the modified formulation was actually reduced from an initial viscosity of 836 cps to a simulated in vivo viscosity of 667 cps, following addition of the phosphate buffered saline solution.

Example 4

As discussed and illustrated below, the viscosity of the compositions of the present invention is affected by the ionic strength of the compositions and pH, as well is as the amounts of tobramycin and xanthan gum selected within the specified ranges of 0.1 to 0.5 w/v % and 0.3 to 0.9 w/v %, respectively. The formulations and associated data presented in Tables 4A-4E are provided to further illustrate and explain the interaction of these factors.

A comparison of Formulations A-D and the respective viscosity values for these compositions illustrates the impact of tobramycin on the viscosity of a composition containing xanthan gum at a concentration of 0.6 w/v %. Specifically, Formulation A, which contains tobramycin at a concentration of 0.3 w/v %, has an initial viscosity of 15 centipoise ("cps"), while Formulation C, which is identical to Formulation A except for the absence of tobramycin, has an initial viscosity of 919 cps. Thus, the presence of tobramycin in Formulation A contributes to the lowering of the viscosity of the composition. This effect of tobramycin is also evident based on a comparison of Formulations B and D. (Formulations A and B do not contain dexamethasone, but are otherwise representative examples of the tobramycin/dexamethasone composi-tions of the present invention. Formulations C and D are provided for comparative purposes and are not representative examples of the compositions of the present invention.)

The viscosity of Formulation A is stabilized by the inclusion of 23.9 mM (0.34%) of sodium sulfate, which is a preferred ionizable species. Formulation A also includes about 10 mM of sodium chloride, as deacetylated xanthan gum stock solution contains sodium chloride, formed by the addition of sodium hydroxide and hydrochloric acid during the deacetylation step. The ionic contributions from EDTA (disodium edetate) and benzalkonium chloride are insignificant, as their concentrations are very low.

The viscosity of Formulation B is stabilized by the inclusion of 138.2 mM sodium chloride, which is also a preferred ionizable species.

The viscosity of the compositions of the present invention can be stabilized using sodium chloride or sodium sulfate. However the concentration of sodium sulfate required is much smaller than the concentration of sodium chloride. Approximately 1 mM of sodium sulfate is equivalent to 5.3 mM of sodium chloride. This is demonstrated by Examples A, B and E though L.

Figure 4:
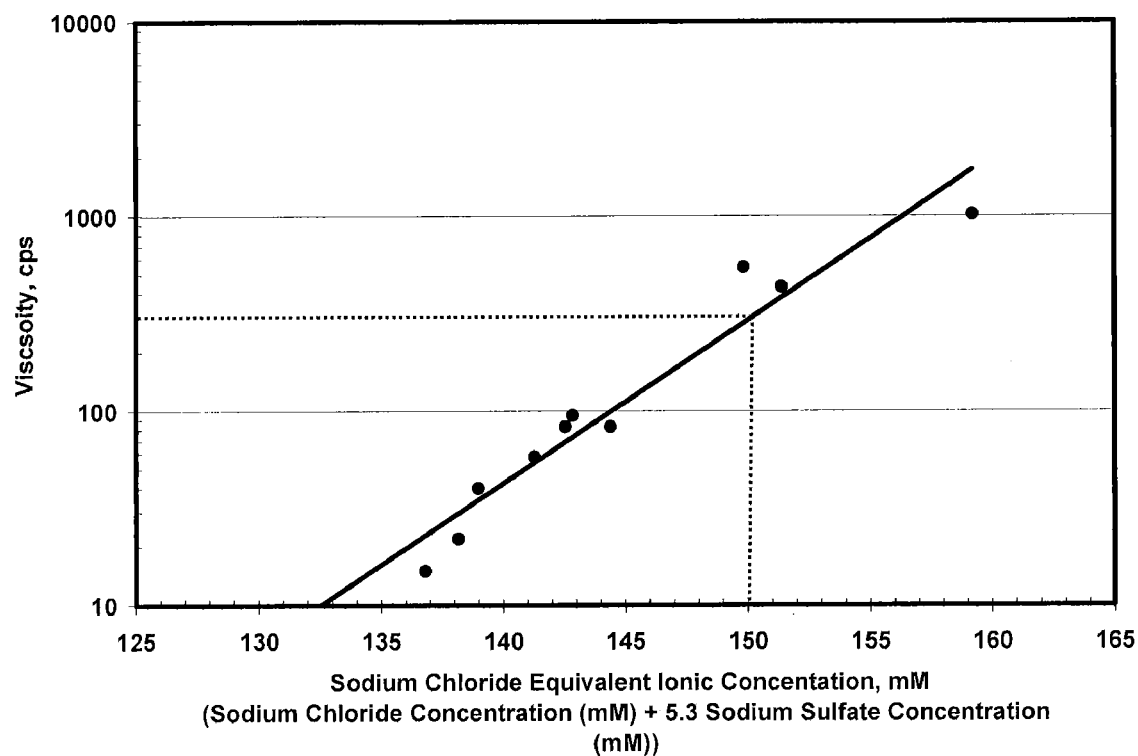
FIG. 4 is a graph illustrating the relationship between sodium chloride equivalent concentration and viscosity, as described in Example 4.

The viscosities of Formulations A, B and E though L versus sodium chloride equivalent ionic concentration is plotted in FIG. 4. The sodium chloride equivalent ionic concentration for these formulations is defined as "sodium chloride concentration (mM)+5.3 sodium sulfate concentration (mM)". The viscosities of the formulations containing 0.3% tobramycin and 0.6% xanthan gum increases as the sodium chloride equivalent ionic concentration increases. The viscosity is in the preferred range of 10 to 300 cps for sodium chloride equivalent ionic concentration range of 134 to 150 mM.

Other ionizable species can be used in place of sodium chloride or sodium sulfate. The preferred ionized salts are sodium chloride, sodium sulfate, sodium citrate, sodium phosphate, sodium borate, sodium acetate, potassium chloride, calcium chloride, and magnesium chloride. The different ionized species will need a different factor (which is 5.3 for sodium sulfate) to determine the sodium chloride equivalent concentration. This factor can be determined by making samples with different ratios of sodium chloride and the other salt. The viscosity results of those samples can then be analyzed to determine the factor for determining the sodium chloride equivalent concentration. This factor will be greater than one for salts with multivalent ions.

For a given active moiety and its concentration, the sodium chloride equivalent ionic concentration range that provides relatively low viscosity depends on pH and xanthan gum concentration. For a 0.3% tobramycin solution, Formulations M and N show that a higher sodium chloride equivalent ionic concentration is required to provide the similar viscosity at lower pH of 5.5 compared to that at pH of 5.75.

Formulations O, P and Q show that at a fixed pH (5.5), lower sodium chloride equivalent ionic concentrations are required as xanthan gum concentration is increased from 0.6% to 0.9%.

TABLE 4A

| | Formulation | | | |
|---|---|---|---|---|
| INGREDIENTS | A W/V % | B W/V % | C W/V % | D W/V % |
| Tobramycin | 0.3 | 0.3 | None | None |
| Xanthan Gum | 0.6 | 0.6 | 0.6 | 0.6 |
| Sodium Chloride | 0 | 0.75 | 0 | 0.75 |
| Sodium Sulfate | 0.34 | 0 | 0.34 | 0 |

TABLE 4A-continued

| INGREDIENTS | Formulation A W/V % | B W/V % | C W/V % | D W/V % |
|---|---|---|---|---|
| Tyloxapol | 0.05 | 0.05 | 0.05 | 0.05 |
| Disodium Edetate | 0.01 | 0.01 | 0.01 | 0.01 |
| Benzalkonium Chloride | 0.01 | 0.01 | 0.01 | 0.01 |
| Propylene Glycol | 0.6 | 0.6 | 0.6 | 0.6 |
| Hydrochloric Acid | Adjust pH to 5.7 | Adjust pH to 5.7 | Adjust pH to 5.7 | Adjust pH to 5.7 |
| Sodium Hydroxide | Adjust pH to 5.7 | Adjust pH to 5.7 | Adjust pH to 5.7 | Adjust pH to 5.7 |
| Purified Water | Qs to 100% | Qs to 100% | Qs to 100% | Qs to 100% |
| Sodium Chloride from Xanthan Stock, mM | 10.0 | 10.0 | 10.0 | 10.0 |
| Sodium Chloride added, mM | 0.0 | 128.2 | 0.0 | 128.2 |
| Total Sodium Chloride Concentration (mM) | 10.0 | 138.2 | 10.0 | 138.2 |
| Sodium Sulfate Concentration (mM) | 23.9 | 0.0 | 23.9 | 0.0 |
| Sodium Chloride concentration (mM) + 5.3 Sodium Sulfate Concentration (mM) | 137 | 138 | 137 | 138 |
| Viscosity at shear rate 6 sec-1 (cps) | 15 | 22 | 919 | 915 |
| Simulated In Vivo Viscosity at shear rate 6 sec-1 (cps) | 783 | 817 | 786 | 786 |
| Viscosity of Formulation as a % of Simulated In Vivo Viscosity | 2% | 3% | 117% | 116% |

TABLE 4B

| INGREDIENTS | Formulation E 12076:14I W/V % | F 12076:17Q W/V % | G 12076:14J W/V % | H 12076:14K W/V % |
|---|---|---|---|---|
| Tobramycin | 0.3 | 0.3 | 0.3 | 0.3 |
| Xanthan Gum | 0.6 | 0.6 | 0.6 | 0.6 |
| Sodium Chloride | 0.1 | 0.55 | 0.23 | 0.35 |
| Sodium Sulfate | 0.3 | 0.1 | 0.25 | 0.2 |
| Tyloxapol | 0.05 | 0.05 | 0.05 | 0.05 |
| Disodium Edetate | 0.01 | 0.01 | 0.01 | 0.01 |
| Benzalkonium Chloride | 0.01 | 0.01 | 0.01 | 0.01 |
| Propylene Glycol | 0.6 | 0.6 | 0.6 | 0.6 |
| Hydrochloric Acid | Adjust pH to 5.7 | Adjust pH to 5.7 | Adjust pH to 5.7 | Adjust pH to 5.7 |
| Sodium Hydroxide | Adjust pH to 5.7 | Adjust pH to 5.7 | Adjust pH to 5.7 | Adjust pH to 5.7 |
| Purified Water | Qs to 100% | Qs to 100% | Qs to 100% | Qs to 100% |
| Sodium Chloride from Xanthan Stock, mM | 10.0 | 10.0 | 10.0 | 10.0 |
| Sodium Chloride added, mM | 17.1 | 94.0 | 39.3 | 59.8 |
| Total Sodium Chloride Concentration (mM) | 27.1 | 104.0 | 49.3 | 69.8 |
| Sodium Sulfate Concentration (mM) | 21.1 | 7.0 | 17.6 | 14.1 |
| Sodium Chloride concentration (mM) + 5.3 Sodium Sulfate Concentration (mM) | 139 | 141 | 143 | 144 |
| Viscosity at shear rate 6 sec-1 (cps) | 40 | 58 | 83 | 83 |
| Simulated In Vivo Viscosity at shear rate 6 sec-1 (cps) | 857 | 823 | 836 | 823 |
| Viscosity of Formulation as a % of Simulated In Vivo Viscosity | 5% | 7% | 10% | 10% |

TABLE 4C

| INGREDIENTS | Formulation I W/V % | J W/V % | K W/V % | L W/V % |
|---|---|---|---|---|
| Tobramycin | 0.3 | 0.3 | 0.3 | 0.3 |
| Xanthan Gum | 0.6 | 0.6 | 0.6 | 0.6 |
| Sodium Chloride | 0.45 | 0.5 | 0.6 | 0 |
| Sodium Sulfate | 0.15 | 0.15 | 0.1 | 0.4 |
| Tyloxapol | 0.05 | 0.05 | 0.05 | 0.05 |
| Disodium Edetate | 0.01 | 0.01 | 0.01 | 0.01 |
| Benzalkonium Chloride | 0.01 | 0.01 | 0.01 | 0.01 |
| Propylene Glycol | 0.6 | 0.6 | 0.6 | 0.6 |
| Hydrochloric Acid | Adjust pH to 5.7 | Adjust pH to 5.7 | Adjust pH to 5.7 | Adjust pH to 5.7 |
| Sodium Hydroxide | Adjust pH to 5.7 | Adjust pH to 5.7 | Adjust pH to 5.7 | Adjust pH to 5.7 |
| Purified Water | Qs to 100% | Qs to 100% | Qs to 100% | Qs to 100% |
| Sodium Chloride from Xanthan Stock, mM | 10.0 | 10.0 | 10.0 | 10.0 |
| Sodium Chloride added, mM | 76.9 | 85.5 | 102.6 | 0.0 |
| Total Sodium Chloride Concentration (mM) | 86.9 | 95.4 | 112.5 | 10.0 |
| Sodium Sulfate Concentration (mM) | 10.6 | 10.6 | 7.0 | 28.2 |
| Sodium Chloride concentration (mM) + 5.3 Sodium Sulfate Concentration (mM) | 143 | 151 | 150 | 159 |
| Viscosity at shear rate 6 sec-1 (cps) | 95 | 433 | 547 | 1016 |
| Simulated In Vivo Viscosity at shear rate 6 sec-1 (cps) | 823 | 811 | 820 | 854 |
| Viscosity of Formulation as a % of Simulated In Vivo Viscosity | 12% | 53% | 67% | 119% |

TABLE 4D

| INGREDIENTS | Formulation M Batch No. 05-39669 W/V % | N Batch No. 05-39450 W/V % |
|---|---|---|
| Tobramycin | 0.3 | 0.3 |
| Dexamethasone | 0.1 | 0.1 |
| Xanthan Gum | 0.6 | 0.6 |
| Sodium chloride | 0.24 | 0.36 |
| Sodium Sulfate | 0.25 | 0.25 |
| Propylene Glycol | 0.6 | 0.5 |
| Tyloxapol | 0.05 | 0.05 |
| Boric Acid | None | None |

TABLE 4D-continued

| | Formulation | |
|---|---|---|
| | M | N |
| | Batch No. | |
| INGREDIENTS | 05-39669 W/V % | 05-39450 W/V % |
| Disodium Edetate | 0.01 | 0.01 |
| Sodium Hydroxide | Adjust pH to 5.75 | Adjust pH to 5.5 |
| Hydrochloric Acid | Adjust pH to 5.75 | Adjust pH to 5.5 |
| Purified Water | Qs to 100% | Qs to 100% |
| Sodium Chloride from Xanthan Stock, mM | 10.0 | 10.0 |
| Sodium Chloride added, mM | 41.0 | 61.5 |
| Total Sodium Chloride Concentration (mM) | 51.0 | 71.5 |
| Sodium Sulfate Concentration (mM) | 17.6 | 17.6 |
| Sodium Chloride concentration (mM) + 5.3 Sodium Sulfate Concentration (mM) | 144 | 165 |
| Viscosity at shear rate 6 sec-1 (cps) | 116 | 151 |
| Simulated In Vivo Viscosity at shear rate 6 sec-1 (cps) | 1059 | 977 |
| Viscosity of Formulation as a % of Simulated In Vivo Viscosity | 11% | 15% |

TABLE 4E

| | Formulation | | |
|---|---|---|---|
| INGREDIENTS | O W/V % | P W/V % | Q W/V % |
| Tobramycin | 0.3 | 0.3 | 0.3 |
| Dexamethasone | 0.1 | 0.1 | 0.1 |
| Xanthan Gum | 0.6 | 0.8 | 0.9 |
| Sodium chloride | 0.36 | 0.23 | 0.1 |
| Sodium Sulfate | 0.25 | 0.25 | 0.25 |
| Propylene Glycol | 0.5 | 0.5 | None |
| Tyloxapol | 0.05 | 0.05 | 0.05 |
| Boric Acid | None | None | 0.5 |
| Disodium Edetate | 0.01 | 0.01 | None |
| Sodium Hydroxide | Adjust pH to 5.5 | Adjust pH to 5.5 | Adjust pH to 5.5 |
| Hydrochloric Acid | Adjust pH to 5.5 | Adjust pH to 5.5 | Adjust pH to 5.5 |
| Purified Water | Qs to 100% | Qs to 100% | Qs to 100% |
| Sodium Chloride from Xanthan Stock, mM | 10.0 | 13.3 | 14.9 |
| Sodium Chloride added, mM | 61.5 | 39.3 | 17.1 |
| Total Sodium Chloride Concentration (mM) | 71.5 | 52.6 | 32.0 |
| Sodium Sulfate Concentration (mM) | 17.6 | 17.6 | 17.6 |
| Sodium Chloride concentration (mM) + 5.3 Sodium Sulfate Concentration (mM) | 165 | 146 | 125 |
| Viscosity at shear rate 6 sec-1 (cps) | 151 | 163 | 636 |
| Simulated In Vivo Viscosity at shear rate 6 sec-1 (cps) | 977 | 1554 | 2208 |
| Viscosity of Formulation as a % of Simulated In Vivo Viscosity | 15% | 11% | 29% |

Example 5

Rabbit Bioavailability Study Results

The ocular bioavailability of three representative compositions of the present invention was evaluated relative to TOBRADEX® (tobramycin 0.3%/dexamethasone 0.1%) Ophthalmic Suspension. The formulations of the compositions of the present invention are shown in Table 5A, below. The formulation of TOBRADEX® Ophthalmic Suspension is shown in Example 1 of U.S. Pat. No. 5,149,694.

TABLE 5A

| | Formulation Number | | |
|---|---|---|---|
| | 109443 W/V % | 109442 W/V % | 108536 W/V % |
| INGREDIENTS | | | |
| Tobramycin | 0.3 | 0.3 | 0.3 |
| Dexamethasone | 0.01 | 0.05 | 0.1 |
| Xanthan Gum | 0.6 | 0.6 | 0.6 |
| Sodium chloride | 0.21 | 0.21 | 0.24 |
| Propylene Glycol | 0.6 | 0.6 | 0.6 |
| Sodium Sulfate (Anhydrous) | 0.25 | 0.25 | 0.25 |
| Tyloxapol | 0.05 | 0.05 | 0.05 |
| Disodium Edetate | 0.01 | 0.01 | 0.01 |
| Benzalkonium Chloride | 0.01 | 0.01 | 0.01 |
| Sodium hydroxide | pH 5.75 | pH 5.75 | pH 5.75 |
| Hydrochloric acid | pH 5.75 | pH 5.75 | pH 5.75 |
| Purified Water | 100% | 100% | 100% |
| RESULTS | | | |
| Viscosity at shear rate 6 sec-1 (cps) | 29 | 32 | 130 |
| Simulated In Vivo Viscosity at shear rate 6 sec-1 (cps) | 872 | 872 | 955 |
| Viscosity of Formulation as a % of Simulated In Vivo Viscosity | 3% | 4% | 14% |

The respective compositions were administered to both eyes of male New Zealand rabbits. Following administration of the formulations, aqueous humor samples were collected from both eyes at 0.5, 0.75, 1, 2, and 3 hours and concentrations of dexamethasone were determined using the LC-MS/MS procedure described below.

Concentrations of dexamethasone in the rabbit aqueous humor were measured using a validated HPLC tandem mass spectrometry (HPLC/MS/MS) method. In this procedure, a 25.0 microliter aliquot of aqueous humor is spiked with beclomethasone as internal standard and extracted using methyl-t-butyl ether. The organic layer is evaporated to dryness and reconstituted in 20:80 10 mM ammonium formate:methanol and injected on a reversed-phase HPLC column under isocratic conditions with a mobile phase of the same composition as used for sample reconstitution. The column effluent is subjected to positive ion electrospray ionization and the protonated molecular ions of dexamethasone and beclomethasone subjected to collisional fragmentation. Multiple reaction monitoring of the m/z 393.1→373.4 and 409.3→391.4 transitions for dexamethasone and beclomethasone, respectively, allows for specific detection. The working range of the procedure is 1.00 to 200 ng/mL.

Figure 5:
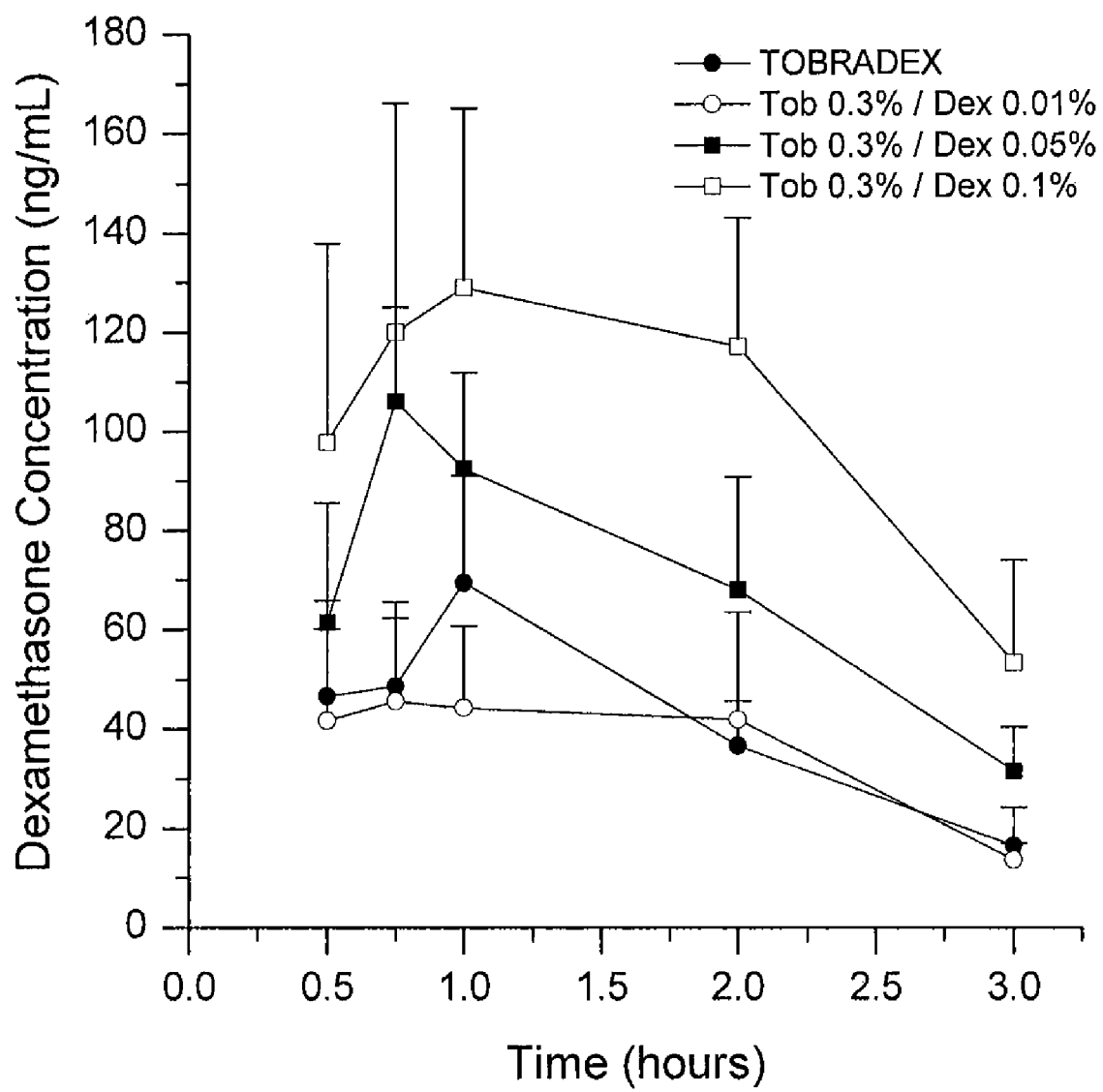
FIG. 5 is a graph showing ocular bioavailability data for three representative formulations of the present invention, in comparison to a prior art formulation, as described in Example 5.

Mean aqueous humor concentrations for dexamethasone versus time are plotted in FIG. 5. The maximum concentrations ($C_{max}$) of dexamethasone in the aqueous humor and area under the curve (AUC) values are provided in Table 5B, below:

TABLE 5B

| Formulation | $C_{max}$ (ng/mL) | $AUC_{0-3\,h}$ (ng*h/mL) |
|---|---|---|
| TOBRADEX ® (tobramycin 0.3%/dexamethasone 0.1% Ophthalmic Suspension) | 69.4 ± 21.6 | 118 ± 6 |
| Formulation 109443 (tobramycin | 45.6 ± 16.6 | 103 ± 9 |

TABLE 5B-continued

| Formulation | $C_{max}$ (ng/mL) | $AUC_{0-3h}$ (ng*h/mL) |
|---|---|---|
| 0.3%/dexamethasone 0.01%) Formulation 109442 (tobramycin 0.3%/dexamethasone 0.05%) | 106 ± 19 | 191 ± 10 |
| Formulation 108536 (tobramycin 0.3%/dexamethasone 0.1%) | 129 ± 36 | 291 ± 14 |

The foregoing results show that the aqueous humor concentrations for the xanthan-based formulations of the present invention, containing dexamethasone at concentrations of 0.05% and 0.1%, respectively, are much higher than those for TOBRADEX® Suspension, which contains 0.1% dexamethasone. These results demonstrate the superior bioavailability of the compositions of the present invention.

I claim:

1. A topical ophthalmic composition, comprising: 0.1 to 0.5 w/v % tobramycin; 0.03 to 0.1 w/v % of dexamethasone; an aqueous, ophthalmically acceptable vehicle containing deacetylated xanthan gum at a concentration of 0.3 to 0.9%; and one or more ionizable species in an amount sufficient to limit ionic interactions between the tobramycin and the deacetylated xanthan gum, such that the in vitro viscosity of the composition is maintained within the range of 10 to 300 cps at a shear rate of 6 $sec^{-1}$ and a temperature of 25° C.; wherein the ionizable species has a sodium chloride equivalent ionic concentration range of 134 to 150 mM; said composition has a pH of 5 to 6.

2. A composition according to claim 1, wherein the one or more ionizable species is selected from the group consisting of inorganic electrolytes, organic buffering agents and combinations thereof.

3. A composition according to claim 2, wherein the one or more ionizable species is selected from the group consisting of sodium chloride, potassium chloride, calcium chloride, magnesium chloride, sodium sulfate, sodium citrate, potassium citrate, sodium phosphate, potassium phosphate, sodium acetate, sodium borate, boric acid/mannitol complexes, boric acid/sorbitol complexes and combinations thereof.

4. A composition according to claim 3, wherein the ionizable species is selected from the group consisting of sodium chloride, sodium sulfate, and combinations thereof.

5. A composition according to claim 1, wherein the composition has an initial viscosity of 25 to 175 cps.

6. A composition according to claim 5, wherein the composition has an in vitro/in vivo viscosity ratio of 0.01 to 0.65.

7. A composition according to claim 6, wherein the one or more ionizable species is selected from the group consisting of inorganic electrolytes, organic buffering agents and combinations thereof.

8. A composition according to claim 7, wherein the one or more ionizable species is selected from the group consisting of sodium chloride, potassium chloride, calcium chloride, magnesium chloride, sodium sulfate, sodium citrate, potassium citrate, sodium phosphate, potassium phosphate, sodium acetate, sodium borate, boric acid/mannitol complexes, boric acid/sorbitol complexes and combinations thereof.

9. A composition according to claim 8, wherein the ionizable species is selected from the group consisting of sodium chloride, sodium sulfate, and combinations thereof.

10. A composition according to claim 9, wherein the composition contains tobramycin at a concentration of 0.3 w/v %, xanthan gum at concentration of 0.6 w/v % and dexamethasone at a concentration of 0.05 w/v %.

11. A composition according to claim 10, wherein the pH of the composition is about 5.7.

12. A method of treating ophthalmic inflammatory conditions wherein either an infection or risk of infection exists, which comprises topically applying a therapeutically effective amount of a composition according to claim 1 to the affected eye.

13. A method of treating ophthalmic inflammatory conditions wherein either an infection or risk of infection exists, which comprises applying a therapeutically effective amount of a composition according to claim 10 to the affected eye.

14. A topical ophthalmic composition, comprising: 0.1 to 0.5 w/v % tobramycin; 0.03 to 0.1 w/v % of dexamethasone; an aqueous, ophthalmically acceptable vehicle containing deacetylated xanthan gum at a concentration of 0.3 to 0.9%; and one or more ionizable species in an amount sufficient to limit ionic interactions between the tobramycin and the deacetylated xanthan gum, such that the in vitro viscosity of the composition is maintained within the range of 10 to 300 cps at a shear rate of 6 $sec^{-1}$ and a temperature of 25° C.; wherein the ionizable species has a sodium chloride equivalent ionic concentration range of 134 to 150 mM; said composition has a pH of 5 to 6; wherein the composition has an in vitro/in vivo viscosity ratio of 0.01 to 0.65.

15. A composition according to claim 14, wherein the ionizable species is selected from the group consisting of sodium chloride, sodium sulfate, and combinations thereof.

16. A composition according to claim 15, wherein the composition contains tobramycin at a concentration of 0.3 w/v %, xanthan gum at concentration of 0.6 w/v % and dexamethasone at a concentration of 0.05 w/v %.

17. A topical ophthalmic composition, comprising: 0.1 to 0.5 w/v tobramycin; 0.03 to 0.1 w/v % of dexamethasone; an aqueous, ophthalmically acceptable vehicle containing deacetylated xanthan gum at a concentration of 0.3 to 0.9%; and one or more ionizable species in an amount sufficient to limit ionic interactions between the tobramycin and the deacetylated xanthan gum, such that the in vitro viscosity of the composition is maintained within the range of 10 to 300 cps at a shear rate of 6 $sec^{-1}$ and a temperature of 25° C.; wherein the ionizable species has a sodium chloride equivalent ionic concentration range of 134 to 150 mM; said composition has a pH of 5 to 6; wherein the one or more ionizable species is selected from the group consisting of sodium chloride, potassium chloride, calcium chloride, magnesium chloride, sodium sulfate, sodium citrate, potassium citrate, sodium phosphate, potassium phosphate, sodium acetate, sodium borate, boric acid/mannitol complexes, boric acid/sorbitol complexes and combinations thereof; wherein the composition has an in vitro/in vivo viscosity ratio of 0.01 to 0.65.

18. A composition according to claim 17, wherein the ionizable species is selected from the group consisting of sodium chloride, sodium sulfate, and combinations thereof.

19. A composition according to claim 18, wherein the composition contains tobramycin at a concentration of 0.3 w/v %, xanthan gum at concentration of 0.6 w/v % and dexamethasone at a concentration of 0.05 w/v %.

* * * * *